United States Patent [19]

Airy et al.

[11] Patent Number: 5,052,379
[45] Date of Patent: Oct. 1, 1991

[54] COMBINATION BRACE AND WEARABLE EXERCISE APPARATUS FOR BODY JOINTS

[75] Inventors: James F. Airy; Thomas D. Kadavy, both of Bellevue, Wash.

[73] Assignee: Soma Dynamics Corporation, Bellevue, Wash.

[21] Appl. No.: 345,035

[22] Filed: Apr. 27, 1989

[51] Int. Cl.⁵ .......................... A61F 3/00; A61F 5/00
[52] U.S. Cl. ............................... 128/80 C; 128/80 F; 128/80 G; 272/130; 272/143
[58] Field of Search ................. 272/67, 132, 129, 130, 272/143; 128/25 R, 78, 80 R, 80 C, 80 F, 80 G

[56] References Cited

U.S. PATENT DOCUMENTS

| | | | |
|---|---|---|---|
| 2,777,439 | 1/1957 | Tuttle | 128/25 |
| 2,832,334 | 4/1958 | Whitelaw | 128/25 |
| 3,373,992 | 3/1968 | Ludeman | 272/130 |
| 3,495,824 | 2/1970 | Cuinier | 272/80 |
| 3,976,057 | 8/1976 | Barclay | 128/25 |
| 4,235,437 | 11/1980 | Ruis et al. | 272/134 |
| 4,354,676 | 10/1982 | Ariel | 272/129 |
| 4,397,308 | 8/1983 | Hepburn | 128/88 |
| 4,407,496 | 10/1983 | Johnson | 272/117 |
| 4,436,303 | 3/1984 | McKillip et al. | 272/132 |
| 4,485,808 | 12/1984 | Hepburn | 128/87 |
| 4,508,111 | 4/1985 | Hepburn | 128/87 |
| 4,520,804 | 6/1985 | DiGeorge | 128/80 |
| 4,538,600 | 9/1985 | Hepburn | 128/88 |
| 4,544,154 | 10/1985 | Ariel | 272/130 X |
| 4,620,532 | 11/1986 | Houswerth | 128/80 C |
| 4,681,097 | 7/1987 | Pansiera | 128/80 C X |
| 4,718,665 | 1/1988 | Airy et al. | 272/132 |
| 4,801,138 | 1/1989 | Airy et al. | 272/130 |
| 4,817,588 | 4/1989 | Bledsoe | 128/80 F X |

FOREIGN PATENT DOCUMENTS 0173161 3/1986 European Pat. Off. .......... 128/80 C
2177603 1/1987 United Kingdom .............. 128/80 C

OTHER PUBLICATIONS

Brochure–The Choice Therapy for a Greater Range of Motion, Dynasplint Systems, Inc. 1988.
Brochure–Now We Go to Any Extremity, Dynasplint Systems, Inc. 1987.

Primary Examiner—Robert Bahr
Assistant Examiner—J. Doyle
Attorney, Agent, or Firm—Christensen, O'Connor, Johnson & Kindness

[57] ABSTRACT

A portable appliance (14) is worn by the user in various configurations, including as a splint to hold a body joint immovable, as a brace to permit the body joint to move through a controlled range of motion and as an exercise apparatus to impart resistance to the flexing and/or extension movement of the body joint. The apparatus (14) includes an articulating frame (16) composed of a first frame section (18) connectable to the first limb of a body joint and a second frame section (20) connectable to a second limb of a body joint. The two frame sections are interconnected together by pivot joint assemblies (22a) and (22b) to permit the frame (16) to articulate about a transverse axis (24) corresponding to the anatomical pivot axis of the body joint. A control plate (164) having adjustable stop pins (166) and (168) is mounted on the pivot joint assemblies to control the range of motion of the articulating frame (16). With the control plate (164) in place, various types of resistance units may be employed to resist relative movement of the frame sections (18) and (20) in either or both directions about the pivot axis (24).

38 Claims, 8 Drawing Sheets

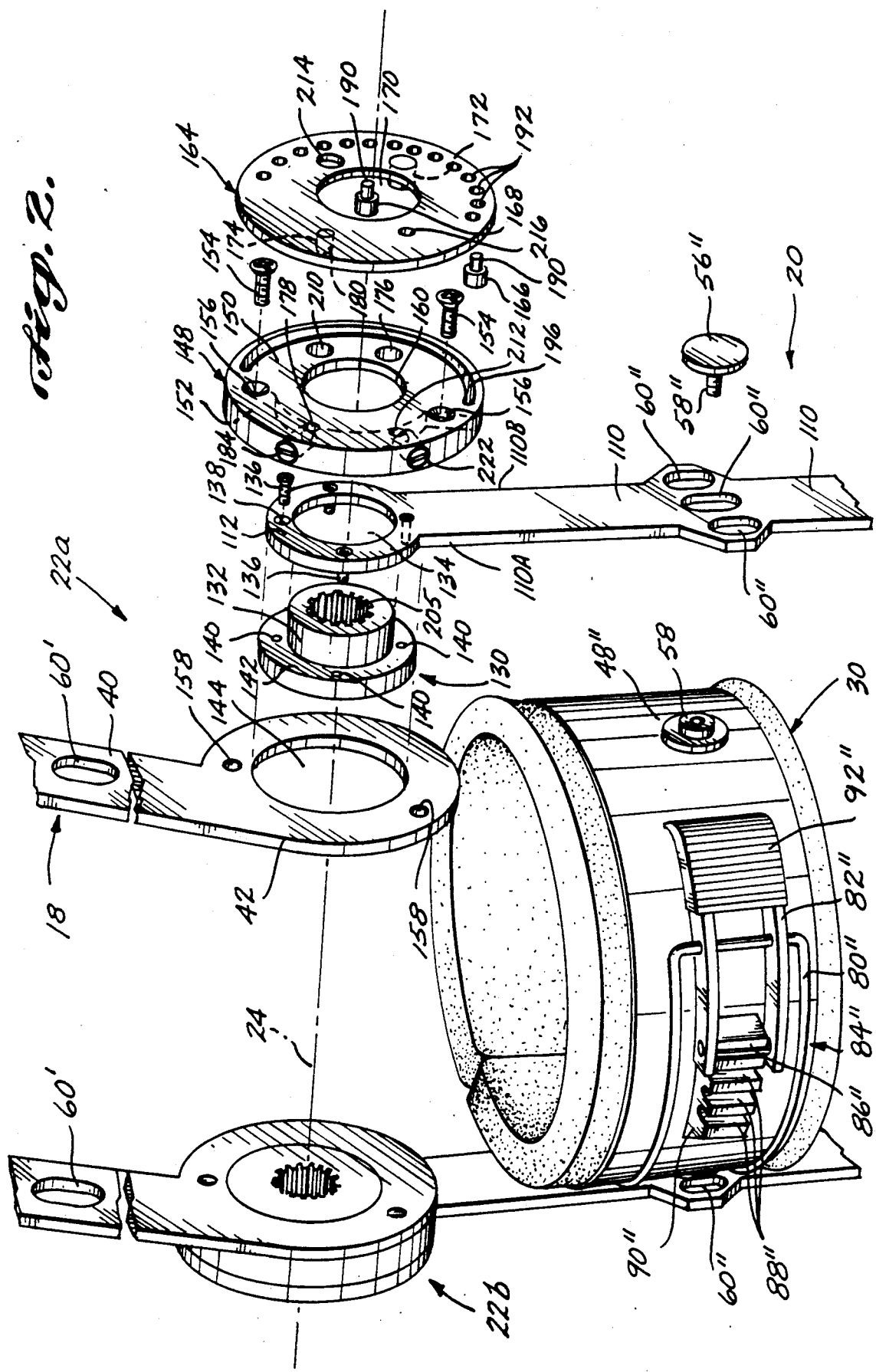

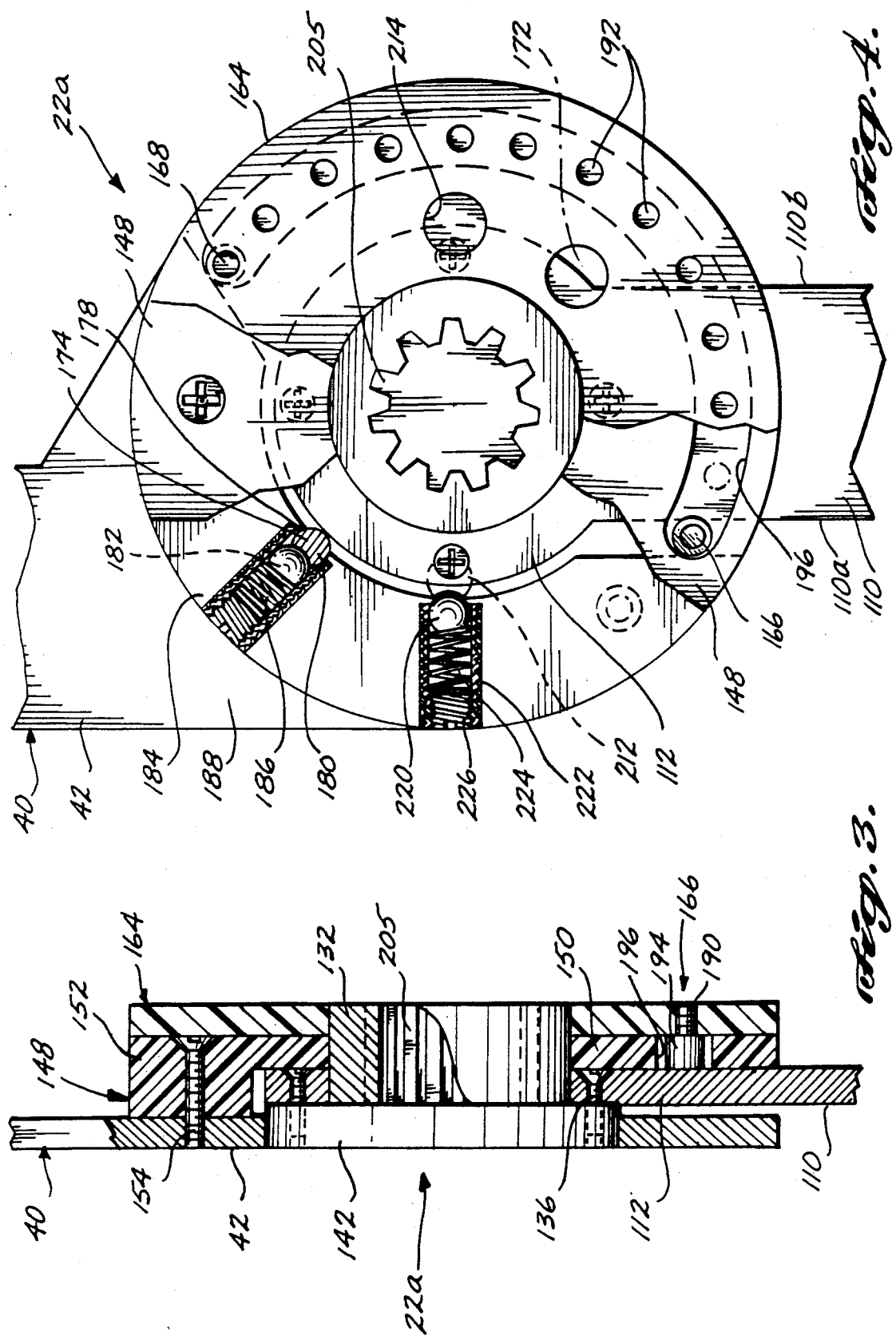

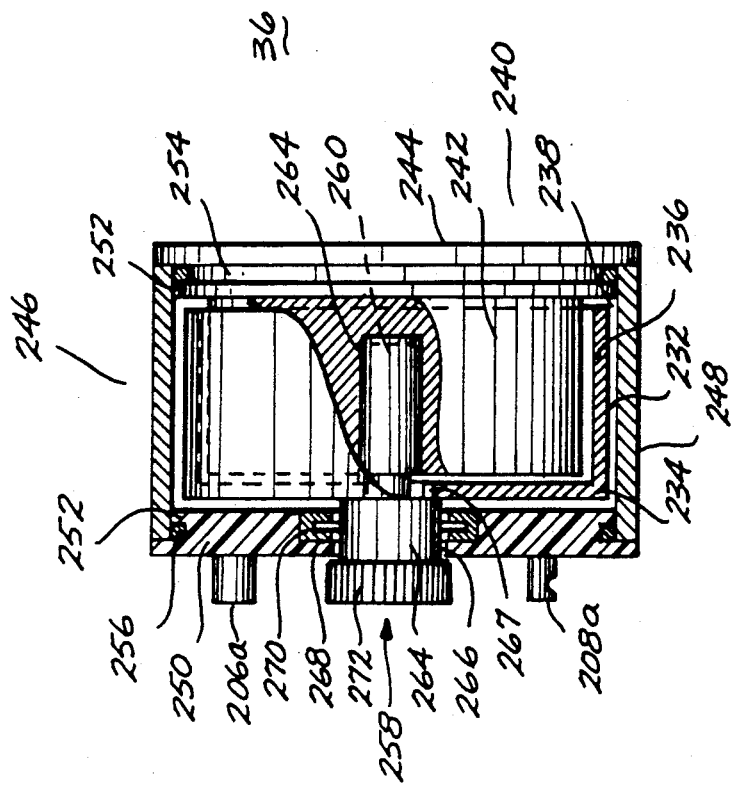
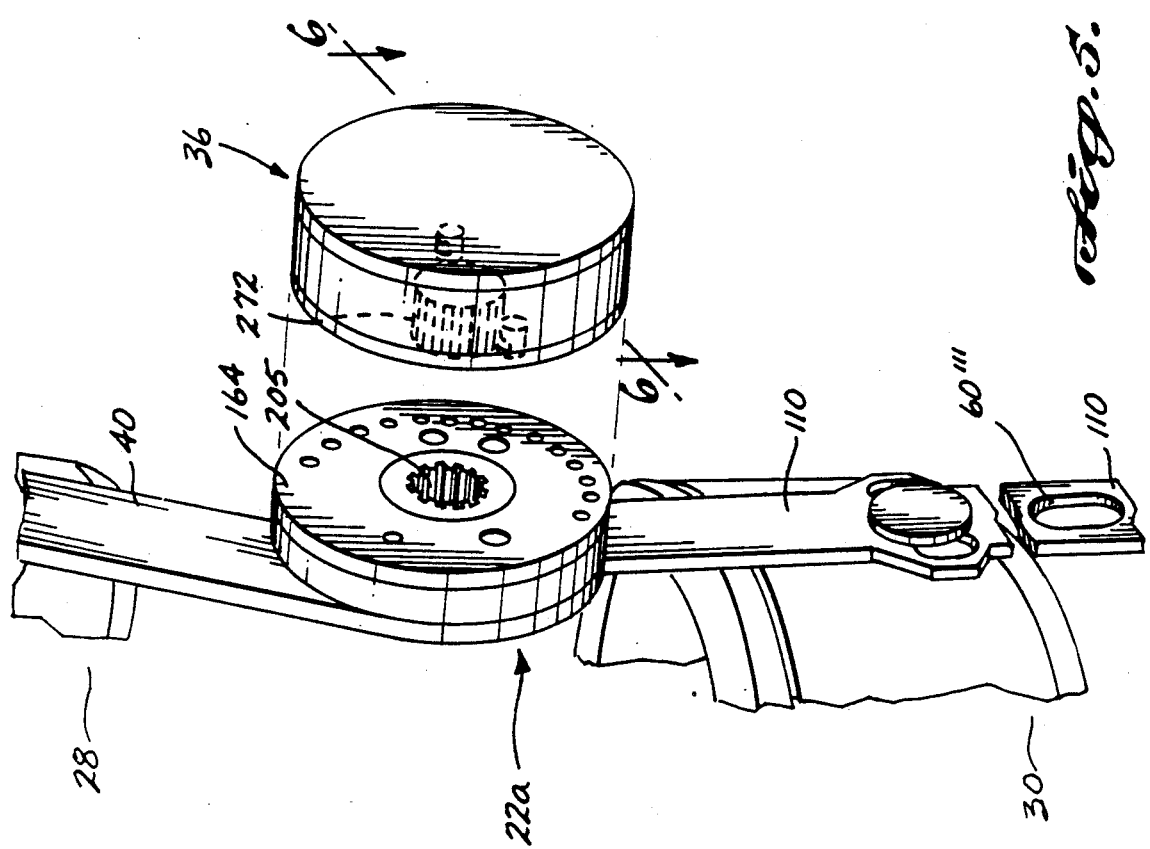

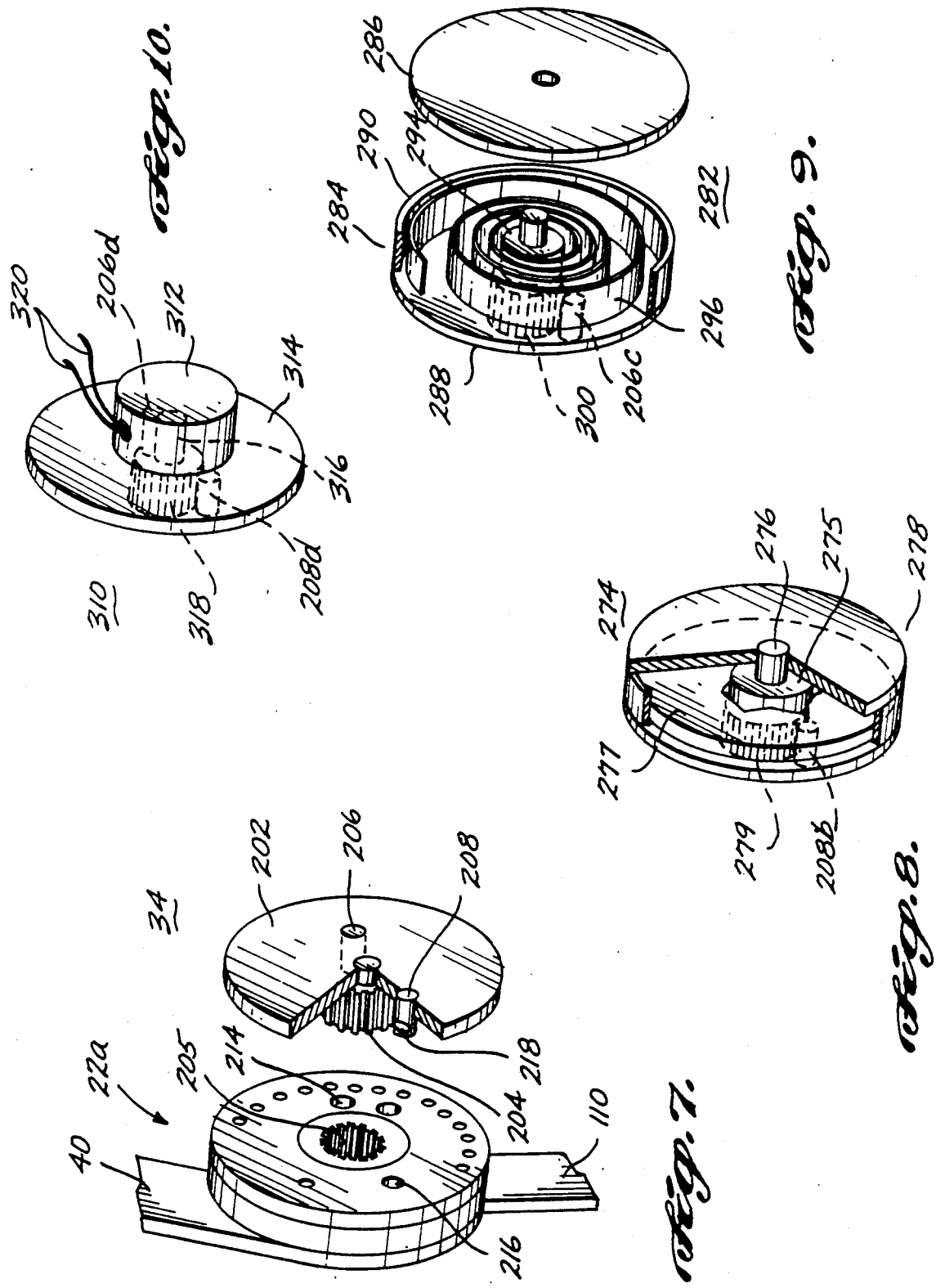

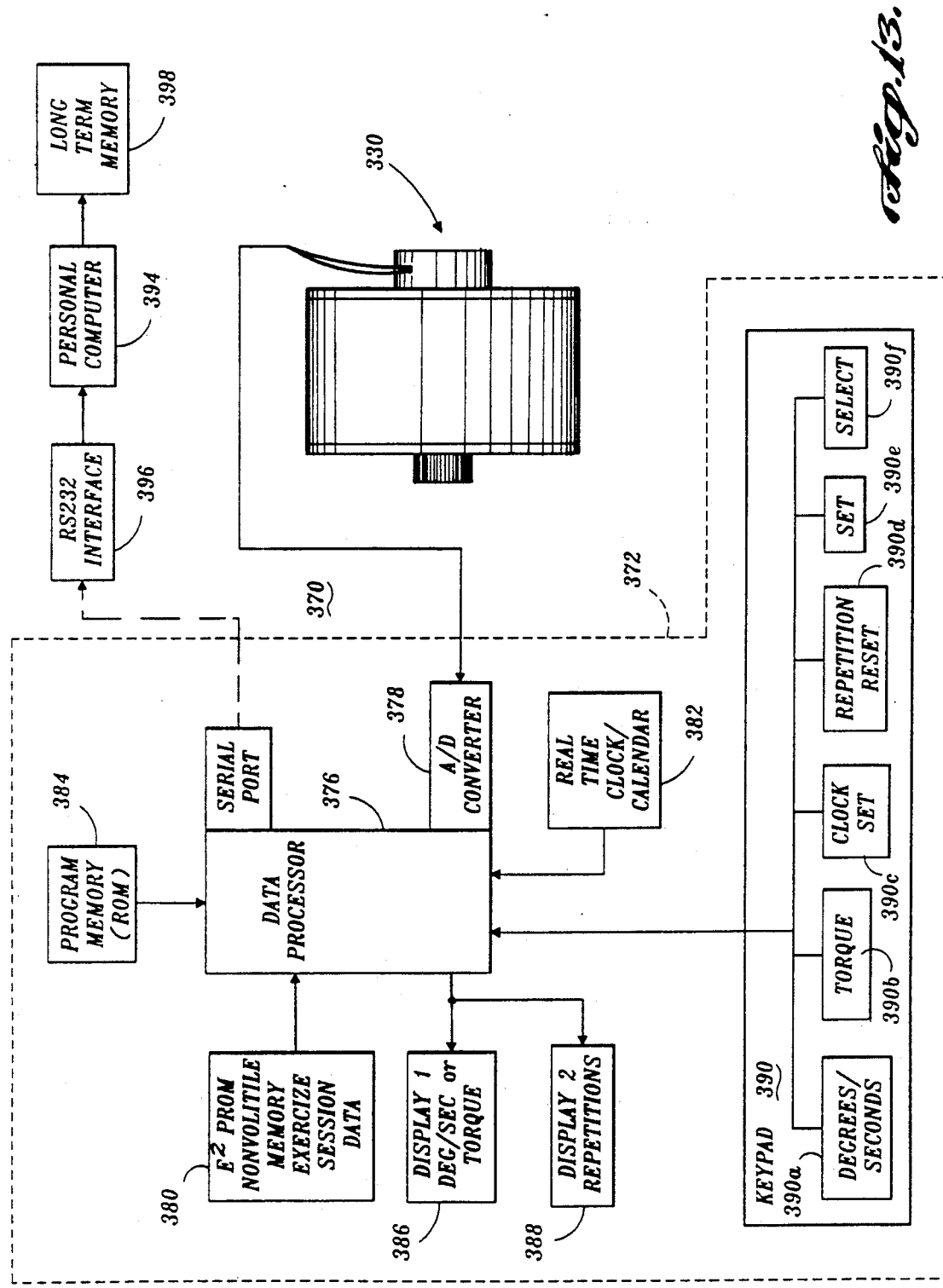

COMBINATION BRACE AND WEARABLE EXERCISE APPARATUS FOR BODY JOINTS

FIELD OF THE INVENTION

The present invention concerns rehabilitation and fitness devices, and more particularly, a combination brace and wearable exercise apparatus which is readily adapted for use in various modes, including as a split to maintain a body joint immovable, as a brace to permit movement of the body joint through a controlled, adjustable range of motion, as an exercise device for exercising the body joint, and also as a test and measurement device for monitoring rehabilitative progress and providing patient feedback.

BACKGROUND OF THE INVENTION

Physical exercise on a regular basis is now a permanent part of the life of millions of people throughout the world. Physical exercise takes many forms, including with the use of numerous types of exercise equipment, for instance, weight machines, rowing machines, exercise bicycles, etc. Also many people participate in rhythmic aerobic exercise of various types, usually with musical accompaniment. In addition, there has been a vast increase in participation in team and individual sports, such as basketball, volleyball, tennis, running and cycling.

Unfortunately, the advent of greater emphasis on physical fitness has resulted in the corresponding increase in musculoskeletal injuries, especially to the knee, ankle, elbow, wrist and other body joints. Not infrequently, surgical procedures are required to repair the damaged or injured muscles, tendons, ligaments, and other components of a body joint. Typically the recovery process requires that the body joint be held immobile for a certain period of time immediately following surgery. This usually necessitates the wearing of a splint. Thereafter, the body joint is allowed to move through a controlled, limited degree of extension and/or flexion, i.e., range of motion. Often a brace or similar appliance is worn to limit the range of motion of the body joint and provide lateral support.

After a period of time, the patient undergoes a therapy regime to rehabilitate the injured body joint. The regime often includes flexing and/or extending the body joint through a controlled range of motion against a selected resistance level, with the range of motion and resistance level typically being increased over time. This treatment is given at the facilities of a physical therapist or clinics specializing in sports-related injuries utilizing sophisticated, expensive machines. To use these machines, the patient must leave his place of employment or home to travel to the office or clinic of the therapist or sports medicine doctor. Examples of specialized, stationary machines that have been designed for conditioning and rehabilitating body joints are disclosed in U.S. Pat. Nos. 2,777,439, 3,495,824, 4,407,496 and 4,436,303.

Some less bulky devices have been developed for exercising or rehabilitating body joints. Such devices typically include two pivotally connected lever arms that are strapped to the limbs of the body joint. A resistance mechanism is utilized to resist the relative movement of the pivot arms and thus impart a resistance force against movement of the body joints. Examples of this type of device are disclosed by U.S. Pat. Nos. 2,832,334, 3,976,057, 4,397,308, 4,485,808, 4,508,111 and 4,538,600 as well as applicants' U.S. Pat. Nos. 4,718,665 and 4,801,138. These devices, however, are not intended to serve as splints in that they do not include a positive method of locking the two lever arms against relative movement. Moreover, such devices are not designed to restrict the movement of the body joint through a controlled range of motion, which range of motion may be selectively adjusted to provide optimum therapeutic characteristics, nor are they designed to provide feedback to the patient/therapist regarding rehabilitative progress. Though adapted to be mounted on the body, these devices are still too cumbersome to be worn continuously through the entire post-operation period and therapy/rehabilitation period.

SUMMARY OF THE INVENTION

The foregoing limitations of known exercise and rehabilitation devices are addressed by the present invention which provides an adjustable combination brace and wearable exercise apparatus to selectively render a body joint immovable, control the movement of the body joint through a desired range of motion, and exercise the muscles associated with the body joint as the body joint is moved through the controlled range of motion and optionally monitor the movement of the body joint and exercise parameters electronically. The apparatus includes a frame structure that is entirely carried by the body. The frame structure is composed of first and second pivot arms that are connected to the first and second limbs of a body joint. A pivot joint assembly interconnects the first and second pivot arms to pivot about an axis generally coinciding with the anatomical pivot axis of the associated body joint. The pivot joint assembly may be adjusted to control the relative angular movement between the first and second pivot arms from a range of substantially no relative angular movement to sufficient angular movement to permit the body joint to pivot between a substantially fully flexed position and a substantially fully extended position.

The pivot joint assembly is also adapted to operably receive replaceable resistance units to impose a desired level of resistance to the movement of the first and second pivot arms in either or both relative rotational directions about the pivot axis of the pivot joint assembly.

In another aspect of the present invention the pivot joint assembly includes a control plate mounted on one of the two pivot arms to carry stop members. The stop members may be placed at selected locations about the control plate, with the location of the stop members on the control plate determining the permitted range of angular motion between the first and second pivot arms.

In a further aspect of the present invention one form of resistance unit usable in conjunction with the pivot joint assembly includes a stator stationarily associated with one of the two pivot arms and a rotor coupled to the other of the two pivot arms to rotate relative to the stator during the relative motion of the two pivot arms. A resistance or drag load is exerted between the rotor and stator that must be overcome to rotate the first and second pivot arms relative to each other. In a particular aspect of the present invention, the drag load is imposed by a high viscosity fluid imposing a fluid shear resistance during relative rotational movement between the stator and rotor.

In an additional aspect of the present invention, a one-way clutch is operably interposed between the rotor and the pivot arm of which the rotor is connected. The one-way clutch functions to drivingly engage the rotor and the associated pivot arm when the associated pivot arm is rotated in a first direction relative to the second pivot arm. Correspondingly, when the associated pivot arm is rotated in the opposite direction relative to the second pivot arm, the rotor and associated pivot arm are drivingly disengaged.

In yet a further aspect of the present invention, the resistance unit imposes a resistance between the first and second pivot arms in one relative direction of movement. The energy required to overcome the resistance is stored by the resistance unit and then expended to assist in rotating the first and second pivot arms in the reverse relative direction tending to return the first and second pivot arms to their nominal positions when the force imposed on the pivot arms to rotate the arms in the first relative direction is terminated.

In yet another aspect of the present invention, the various physical parameters are monitored by a transducer that may be interfaced by a microprocessor thereby to provide data about rehabilitative process and the exercise session, including for instance, the range of movement of the body joint, the speed at which the body joint is flexed and extended, the effort being expended by the body joint to overcome the resistance unit, etc.

In yet an additional aspect of the present invention, the data provided by the transducer is transmitted to a data recorder and microprocessor housed in a hand-held unit that may be detachably connected to the transducer. The data recorder/microprocessor not only stores the information received from the transducer, but also calculates in real time various physical values, including the speed of relative movement between the first and second pivot arms and the torque being expended during the relative movement of the two pivot arms. Another value that is calculated is the number of cycles of the present invention when used as an exercise or rehabilitation apparatus. Periodically the hand-held data recording/microprocessor unit may be interfaced with a personal computer to down load the data stored in the hand-held unit and also to utilize the data to analyze the progress of the patient/exerciser using more sophisticated techniques than possible with the hand-held unit.

BRIEF DESCRIPTION OF THE DRAWINGS

The details of typical embodiments of the present invention will be described in connection with accompanying drawings, in which:

FIG. 2 is an enlarged, fragmentary isometric view of the present invention shown in FIG. 1, with certain components exploded to more specifically illustrate the construction of the pivot joint assembly;

FIG. 3 is an enlarged, fragmentary, partial cross-sectional view of the pivot joint assembly shown in FIG. 1 and taken substantially along lines 3—3 thereof;

FIG. 4 is an enlarged, fragmentary, elevational view of the present invention shown in FIG. 3 with portions broken away to more specifically illustrate the construction of the pivot joint assembly;

FIG. 5 is a fragmentary, isometric view of the present invention utilizing a viscous resistance unit to apply a resistance force to the movement of the body joint;

FIG. 6 is a partial cross-sectional view of the resistance unit shown in FIG. 5 and taken substantially along lines 6—6 thereof;

FIG. 7 is a fragmentary, isometric view of the present invention utilizing a stop plate unit, with portions broken away, illustrating the use of the present invention as a splint;

FIG. 8 is an isometric view with portions broken away of a further resistance unit employable with the present invention;

FIG. 9 is an isometric view of an additional resistance unit with portions broken away and exploded;

FIG. 10 is an isometric view of a measurement module for measuring various parameters associated with the use of the present invention in conjunction with a body joint;

DETAILED DESCRIPTION OF THE PREFERRED EMBODIMENTS

Figure 1:
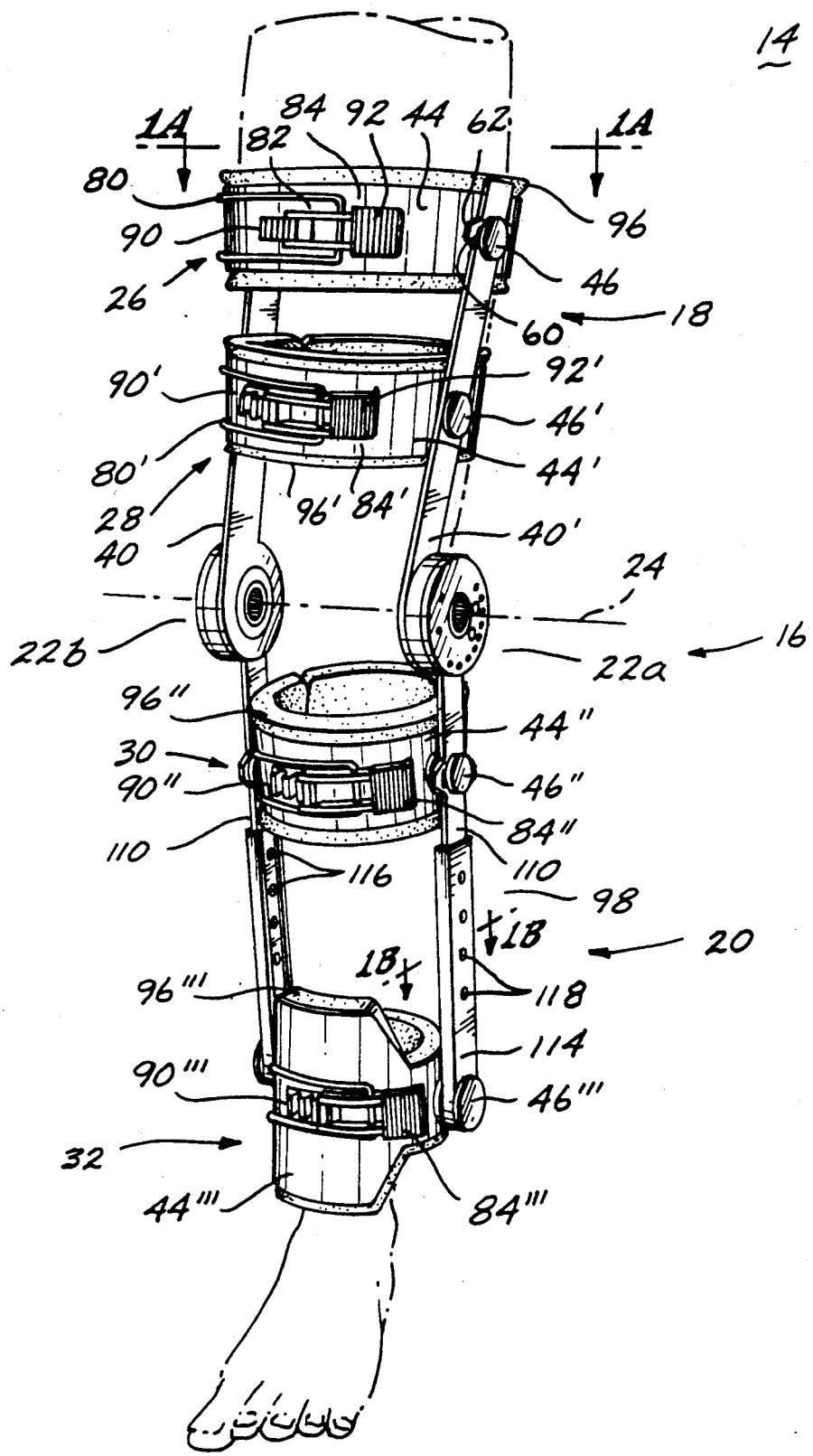
FIG. 1 is an isometric view of the present invention adapted for use with the knee joint.

Referring initially to FIG. 1, a combination brace and portable body joint exercising appliance or apparatus 14 is illustrated for use in conjunction with a knee joint. However, it is to be understood that the present invention may be adapted for use in conjunction with other body joints, such as the ankle, elbow or wrist. As shown in FIG. 1, in basic form, the apparatus 14 includes an articulating frame 16 composed of an upper frame section 18 connected to a lower frame section 20 by pivot joint assemblies 22a and 22b to enable the upper and lower frame sections to relatively pivot or articulate about a transverse axis 24. The pivot axis 24 is positioned in approximate alignment with the anatomical axis of rotation of the knee by a pair of upper cuff assemblies 26 and 28 of the upper frame section 18 to encircle the wearer's thigh and a pair of lower cuff assemblies 30 and 32 of the lower frame section 20 to encircle the lower leg of the wearer.

The present invention may be readily reconfigured depending upon the desired usage. For instance, as shown in FIGS. 1 through 4, the apparatus 14 may be used as a brace to permit the wearer to flex and extend his leg through a preset range of motion. Alternatively, a lock-up plate assembly 34 shown in FIG. 7 may be mounted on the pivot joint assemblies 22a and 22b to prevent any relative motion between the upper frame section 18 and the lower frame section 20. In this configuration, the apparatus 14 may be utilized as a splint. The lock-up plate assembly 34 may be conveniently removed from the pivot joint assemblies 22A and 22B and substituted with a resistance load unit or mechanism 36 shown in FIGS. 5 and 6 to apply desired levels of resistance to relative rotation of the upper and lower frame sections 18 and 20 during flexure and/or extension of the leg. The knee joint is exercised simply by flexing and extending the leg in opposition to the resistance load mechanism 36. Simultaneously, the pivot joint assemblies 22a and 22b may be adjusted to allow the leg to pivot about the knee joint along a controlled range of motion in response to various factors, including the nature of the injury sustained by the knee, the stage of rehabilitation of the knee, etc.

The following will describe the construction and operation of the combination brace/exercise apparatus 14 in more detail. In the ensuing description, the term "inward" shall mean toward the longitudinal central axis of the wearer's leg with the term "outward" meaning in the opposite direction. The term "front" shall correspond with the anterior portion of the wearer's leg, whereas the term "rear" shall correspond with the posterior of the wearer's leg.

As most clearly shown in FIGS. 1, 1A, 2 and 3, the upper frame section 18 of the pivot frame 16 include a pair of flat, elongate upper arms 40 extending upwardly from lower, enlarged, circular cheek plate portions 42 to support the upper cuff assemblies 26 and 28 at the sides of the leg. Specifically referring to FIGS. 1 and 1A, the uppermost cuff assembly 26 includes an outer shell 44 composed of hard, flexible material that does not appreciably stretch or compress but which is readily formed into a circular shape to circumferentially encircle the wearer's thigh. Examples of materials that may be employed to form the outer shell 44 include hard plastic materials and thin, flexible metallic materials.

Figure 1A:
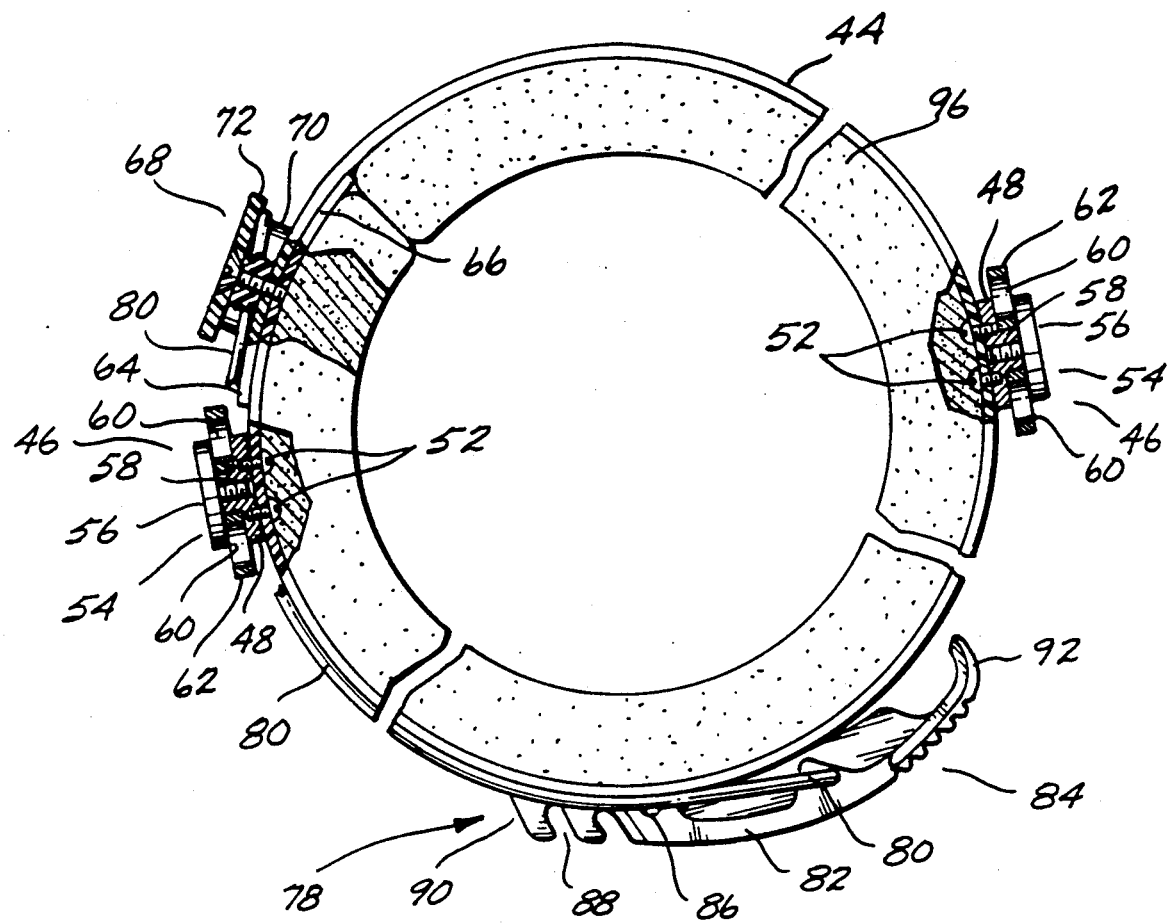
FIG. 1A is an enlarged, cross-sectional view of the present invention shown in FIG. 1 taken substantially along lines 1A—1A thereof, specifically illustrating the construction of the uppermost cuff assembly.

Pin assemblies 46 are mounted on diametrically opposite side portions of the outer shell 44 to mount the shell on the upper arms 40. The pin assemblies 46 include an inward section 48 secured to the outer side of the outer shell 44 by hardware members 52 extending through clearance holes formed in the outer shell to engage the pin inward sections 48. The pin assemblies 46 also include outward sections 54 having an enlarged outer head portion 56 and a smaller diameter shank portion 58 engageable through one of three side-by-side, spaced apart clearance holes 60 formed in the upper arm 40 adjacent the free end thereof, to threadably engage a corresponding pin inward section 48. As illustrated in FIGS. 1 and 1A arcuate flanges 62 extend laterally from the side edge portions of the upper arms 40 to accommodate the clearance holes 60. The head portions 56 of the pin outward sections 54 are sufficiently larger than their corresponding shank portions 58 to serve as a bearing surface against upper arms 40. It will be appreciated that the circumferential size of the outer shell 44 may be adjusted by the particular clearance holes 60 in which the pin outward section 54 is placed so as to accommodate wearers having thighs of different girths. It will also be appreciated that use of the pin assemblies 46 and the holes 60 to mount the uppermost cuff assembly 26 on the upper frame section 18 allows the cuff assembly to pivot relative to the upper arms 40. This enables legs of different shapes and sizes to be accommodated.

As illustrated in FIG. 1A, the outer shell 44 is constructed in "split" design having end portions that overlap each other at a location corresponding to the rearward and outward portion of the wearer's leg. This enables a wearer to conveniently enter the cuff assembly 26 from the rear of the apparatus 10. Preferably, the outer shell 44 is constructed with a longer free end portion 64 that extends around the rear of the wearer's leg to overlap a shorter free end 66 of the cuff. An anchor button 68 is mounted on the longer cuff free end 64 by any appropriate means. The anchor button 68 includes a smaller diameter shank portion 70 adjacent the outer surface of the cuff free end 64 and an enlarged head portion 72 spaced away from the outer surface of the shell free end portion 64.

A "quick release" buckle assembly 78 is provided to maintain the uppermost cuff assembly 26 tightly wrapped around the wearer's leg. The buckle assembly 78 includes a looped line strap 80 pivotally engaged with the curve side members 82 of an "over-center" type latch 84 at locations intermediate the ends of the side members. The opposite end of the line strap 80 is engageable with the anchor button 68, with the enlarged head portion 72 of the button retaining the line strap engaged with the button. The latch 84 also includes a pivot bar 86 spanning the side members 82 at one end of the latch for engagement within one of a series of spaced apart grooves 88 of a catch 90 mounted on the outer shell 44 at a location on the forward side of the outer shell. A manually graspable handle 92 spans across the curved side members 82 of the latch 84 at the ends of the side members opposite the pivot bar 86. With the line strap 80 engaged with an anchor button 68, the pivot bar 86 is engaged within a desired catch groove 88 (depending on the girth of the wearer's leg) and then the latch 84 is pivoted about the bar 86 until the handle 92 is adjacent the cuff outer shell 44 whereupon the latch 84 will be in "over center" position thereby locking the latch in place.

Resilient padding 96 is mounted on the inside surface of the outer shell 44 to provide comfort to the wearer and to snugly fit the cuff assembly 26 around the leg. The padding may be composed of appropriate resilient materials such as foamed rubber or plastic.

As illustrated in FIG. 1, apparatus 14 includes an upper cuff assembly 28 spaced between the uppermost cuff assembly 26 and the transverse pivot axis 24. The cuff assembly 28 is constructed similarly to the uppermost cuff assembly 26 and thus, their corresponding components are given the same numeric designation but with a "prime (')" added. One difference in cuff assembly 28 is that it is mounted on oblong holes 60' extending longitudinally of the upper arms 40, see FIG. 2. As a result, the cuff assembly 28 is adapted not only to pivot relative to the upper arm 40 about a transverse axis, but also to slide toward and away from the pivot axis 24 of the frame 16 as the body joint is being flexed or extended, as discussed more fully below.

Figure 1B:
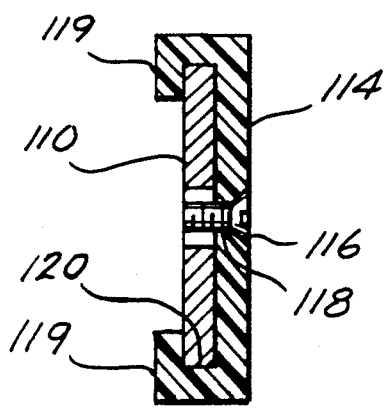
FIG. 1B is an enlarged, cross-sectional view of the present invention shown in FIG. 1 taken substantially along lines 1B—1B thereof, specifically illustrating the construction of the telescoping lower leg assembly.

As shown in FIGS. 1 and 1B the lower frame section includes a pair of adjustable length arm assemblies 98, with each composed of a flat, substantially straight, relatively thin lower arm 110 extending downwardly from an enlarged, generally circular cheek plate section 112. The lower arms 110 engage with elongate, substantially straight extension members 114. A pair of longitudinally spaced apart through holes are formed in the lower arms 110 to receive hardware members 116 that extend through aligned, spaced apart through holes 118 formed in the extension members 114 so that the upper portion of the extension members 114 outwardly overlap the lower ends of the lower arms 110. It will be appreciated that the particular openings 118 through which the hardware members 116 are engaged determine the overall length of the lower arm assemblies 98. Preferably, in cross section, the extension members 114 are generally channel-shaped, having flange portions 119 to cooperatively define an undercut channel 120 to captively and slidably receive a coresponding lower arm 110. By this construction, the extension members 114 and lower arms 110 are maintained in longitudinal alignment with each other while permitting these components to be readily telescopically adjusted relative to each other to increase or decrease the overall length of the lower arm assemblies 98 as desired.

A first lower cuff assembly 30 is mounted on the lower arms 110 of the lower frame section 20 similarly to the manner in which the upper cuff assembly 26 is mounted on the upper frame section 18 with the exception that the cuff assembly is mounted on oblong holes 60" formed in sets of three and extending longitudinally of the lower arms 110. As a result, the cuff assembly 30 is capable of rotating relative to the lower arm assemblies 98 about a transverse axis and also sliding (floating) longitudinally of the lower arms 110 toward and away from the transverse axis 24. The components of the cuff assembly 30 corresponding to the construction of the upper cuff assemblies 26 and 28 are indicated with the same part number but with a "double prime (")" designation.

In a manner similar to upper cuff assembly 28, the lower frame section 20 includes a lowermost cuff assembly 32 which is mounted on the extension members 114 and adapted to pivot about a transverse axis and also "float" toward and away from the pivot axis 24 within oblong holes 60'" formed in the lower end portions of the extension members as shown in FIG. 5. The components of the lower cuff assembly corresponding to the cuff assemblies 26, 28 and 30, are designated by the same part number, but with a "triple prime ('")" designation. Preferably the outer shell 44'" of the cuff assembly 32 is shaped to extend upwardly and downwardly from the nominal width of the outer shell at the front portion thereof thereby to overlap a significant portion of the wearer's shin. This increased bearing area between the cuff assembly 32 and the shin helps to maintain the cuff assembly stationary with the wearer's lower leg portion without discomfort to the wearer.

As discussed above, the cuff assemblies 28, 30, and 32 are mounted on the frame 16 by respective pin assemblies 46', 46", and 46'" extending through oblong holes 60', 60", and 60'". As a result, the cuff assemblies 28, 30, and 32 are permitted to "float" along the frame 16 toward and away from the transverse pivot axis 24 of the frame whereas the uppermost cuff assembly 26 is not permitted to move toward and away from the transverse axis. By this construction, the uppermost cuff assembly 26 is utilized to "stationarily" mount the apparatus 14 on the wearer's leg whereas the remaining three cuff assemblies, though being securely wrapped around the wearer's leg, by being movable toward and away from the pivot axis 24, enable the brace of the present invention to accommodate legs of different shapes and sizes as well as the fact that it is not always possible to align the pivot axis 24 at precisely the anatomical pivot axis of the knee joint. Moreover, no matter how tight the uppermost cuff assembly 26 is secured around the wearer's thigh, during use the apparatus 14 may shift somewhat relative to the leg. Thus, the cuff assemblies 28, 30, and 32 are designed to provide lateral support for the wearer's leg and knee joint while taking into consideration the reality that human legs are not all of the same shape and size and that misalignment between the pivot axis 24 and the anatomical axis of the knee joint may occur, without imposing pistoning forces on the knee joint is the leg is flexed and/or extended.

Also by enabling the cuff assemblies 28, 30, and 32 to float relative to the transverse axis, the present invention accommodates the fact that a knee joint approximates but is not exactly analogous to a simple hinge joint. In reality, as the leg is flexed or extended, the anatomical pivot axis moves rearward and forward, respectively, of the leg. Applicants' manner of mounting the cuff assemblies on the frame 16 enables the transverse axis 24 to shift in the fore and aft direction in response to the fore and aft movement of the anatomical pivot axis of the knee joint. As will be appreciated, this lessens the likelihood that undesirable transverse loads will be imposed on the knee joint in the fore and aft direction during the use of the present invention.

It will be appreciated that the cuff assemblies 26, 28, 30, and 32 may be of other configurations without departing from the spirit or scope of the present invention. For instance, the cuff assemblies can be constructed of a two-piece shell, not shown, having a forward section extending circumferentially sufficiently around the front and sides of the leg to be mounted on the upper and lower frame sections 18 and 20 by the pin assemblies 46. The cuff assemblies may also include a rearward section sized to extend circumferentially around a majority of the rear of the leg but with a gap at each end adjacent the corresponding ends of the forward section. The rearward section may be mounted on a looped line strap similar to strap 80, with such line strap extending circumferentially along the entire length of the rearward section to engage an anchor button, similar to the anchor button 68, mounted on the portion of the front section diametrically opposite the buckle assembly 78.

Next referring specifically to FIGS. 2-4, the pivot joint assemblies 22a and 22b will be described in further detail. It is to be understood that these two pivot joint assemblies are essentially identical in construction, and thus only pivot joint assembly 22a will be described in detail, with the understanding that the pivot joint 22b is essentially identically constructed.

The circular cheek plate 42 formed at the lower end of upper arm 40 constitutes an integral portion of the pivot joint assembly 22a. The cheek plate 42 is offset relative to the upper arm section 40 in the rearward direction in a manner similar to which the lower end of a femur bone is offset rearwardly. In this manner, the transverse pivot axis 24 of the pivot joint assemblies 22a and 22b is located at or very near the anatomical rotational axis of the knee joint. It will be appreciated that when utilizing the present invention in conjunction with other body joints, it may be desirable to offset the cheek plate 42 in the opposite (forward) direction from that shown in FIGS. 2 and 4 or perhaps to centrally align the cheek plate with the upper arms 40.

The upper frame section 18 is pivotally connected to the lower frame section 20 by a stub shaft 130 having a shaft portion 132 that is closely receivable within a circular opening 134 centrally formed in the cheek plate section 112 of the lower arm 110. The stub shaft 130 is securely attached to the cheek plate section 112 by threaded hardware members 136 that extend through clearance holes 138 formed in the cheek plate section 112 to engage with aligned threaded holes 140 extending into the adjacent face of an enlarged, circular flange portion 142 of the stub shaft 130. The outer diameter of the enlarged flange portion 142 is sized to closely and rotatably engage within a circular opening 144 centrally formed in the cheek plate 42 of the upper arm 40.

The flange 142 is maintained in engagement within the circular opening 144 while permitting articulation of the upper arm 40 relative to the lower arm assembly 98 by a generally circular, disc-shaped support plate 148. The support plate 148 has a major disc section 150 and an inwardly directed, arcuate shoulder or boss 152 extending around the portion of the circumference of the disc section 150. The shoulder 152 bears against a corresponding portion of the cheek plate 42 of the upper arm 40. The support plate 148 is securely mounted on the cheek plate 42 by a pair of hardware members 154 that extend through clearance openings 156 formed in the support plate to engage within aligned threaded openings 158 formed in the cheek plate. The support plate 148 is formed with a circular, central bore 160 to closely and rotatably receive and support the shaft portion 132 of the stub shaft 130. It will be appreciated that by the foregoing construction the cheek plate section 112 of lower arm 110 is held captive between the support plate 148 and the cheek plate portion 42 of upper arm 40 while permitting the lower arm to pivot relative to the upper arm. Ideally, the outer diameter of the control plate 48 corresponds to the outer diameter of the cheek plate 42 not only for visual appearance, but also to eliminate any ridges or "high spots" that might impinge on the wearer or the wearer's clothing.

The arc through which the lower arm assembly 98 is permitted to articulate relative to the upper arm 40, and thus the range of motion of a wearer's leg, is controlled by a removable control plate 164 together with moveable stops 166 and 168. The control plate 164 is in the form of a thin, flat circular disc having an outside diameter corresponding to the outside diameter of the support plate 148 and a central through bore 170 ideally of the same size or slightly larger than the through bore 160 of the support plate. The control plate 164 is anti-rotationally mounted on the support plate 148 by two diametrically opposed stub pins 172 and 174 that engage with corresponding, aligned bores 176 and 178 extending through the support plate 148. Ideally, the stub pins 172 and 174 are of different diameters to insure that the control plate 164 is mounted on the support plate 148 in the correct orientation, as shown in FIGS. 2 and 4. A generally V-shaped or arcuate notch 180 is formed on the smaller diameter stub pin 174 to engage with a ball 182 disposed within a cross bore 184 extending diametrically inward from the outer circumference of the support plate 148 to intersect the through bore 178 corresponding to the stub pin 174. The ball 182 preferably is larger than the diameter of the bore 178 so as to be held captive within the cross bore 184. Also ideally the ball 182 is resiliently loaded by a compression spring 186, with the load on the spring adjustably maintained by a threaded hardware member in the form of a set screw 188, which may be engaged within the cross bore 184 to a desired depth. It will be appreciated that the ball 182 and notch 180 serve as a detent arrangement to secure the control plate 164 on the support plate 148 while enabling the control plate 164 to be conveniently lifted away from the support plate when desired without having to unscrew or disassemble any hardware or other components.

The range of articulation between the upper arm 40 and the lower arm assembly 98 is controlled by the stop pins 166 and 168, each having a stub shaft portion 190 sized to engage within an array of spaced-apart through holes 192 formed in the control plate along a circumferential arc. The stop pins 166 and 168 also include an enlarged, circular head portion 194 designed to abut against the side edges of the lower arm 110 to prevent further rotation of the lower arm relative to the upper arm 40. An arcuate clearance slot 196 extends along the outer periphery of the support plate 148 coinciding with the location of the through holes 192 to provide clearance for the head portions 194 of the stop pins 166 and 168.

It will be appreciated that the stop pin 166 is designed to abut against the forward side edge 110a of the lower arm 110 to limit the extension of the wearer's leg, whereas the stop 168 is designed to abut against the rearward side edge 110b of the lower arm to limit the flexion of the wearer's leg. The maximum degree of extension and flexion, and thus the range of motion of the wearer's leg, may be selectively controlled by the particular holes 192 in which the stops 166 and 168 are placed. In this regard, the stops 166 and 168 may be quickly and conveniently relocated by simply removing the control plate 164 from the support plate 148 and then removing the stop pin 166 and/or the stop pin 168 from their current through hole(s) 192 and then reinserting the stop pin(s) in a different through hole. It will be appreciated that a sufficient number of holes 192 are arranged along a sufficiently long arc to enable the wearer's leg to be fully flexed and fully extended if desired. Moreover, the stop pins 166 and 168 may be positioned closely adjacent their corresponding side edges 110a and 110b of the lower arm 110 to restrain the lower arm from virtually any rotational movement relative to the upper arm 40. In this mode, the present invention may be utilized as a splint.

Rather than relying solely on the stop pins 166 and 168 to maintain the lower arm assembly 98 stationary relative to the upper arm 40, a "positive" lock-up is achieved by utilizing the locking plate assembly 34 shown in FIG. 7. The locking plate assembly 34 includes a flat, thin, circular locking plate 202 having an outside diameter corresponding to the diameter of the control plate 164. A male spline 204 is centrally mounted on the inside surface of the locking plate 202 to engage with corresponding female splines 205 formed in the inside diameter of the stub shaft 130 when the locking plate 202 is engaged in face-to-face relationship with the outside surface of the control plate 164. In this regard, stub pins 206 and 208 extend transversely from the inside surface of the locking plate to engage within corresponding diametrically opposed, aligned bores 210 and 212 formed in the support plate 148. The bores 210 and 212 preferably are identical to corresponding bores 176 and 178, described above. Likewise, stub pins 206 and 208 are essentially identical with corresponding stub pins 172 and 174, described above, but with the exception that the stub pins 206 and 208 are somewhat longer to accommodate the thickness of the control plate 164. Clearance holes 214 and 216, aligned with reception bores 210 and 212, are formed in the control plate 164 to provide clearance for the stub pins 206 and 208. As with stub pin 174, stub pin 208 includes a generally V-shaped notch 218 for receiving a detent ball 220 disposed within a cross-bore 222 extending radially inwardly from the outer circumference of the support plate 148 in alignment with the bore 212. As with detent ball 182, ideally the detent ball 220 is larger in diameter than the stub pin bore 212 to maintain the detent ball captive within the cross-bore 222. The detent ball 220 is resiliently loaded by a compression spring 224 which is preloaded by a set screw 226 which engages within corresponding threads formed in a cross hole 222.

It will be appreciated that by the foregoing construction the lock-up plate assembly 34 functions as a positive lock to prevent relative angular movement between the lower arm assembly 98 and the upper arm 40. In addition, the locking plate assembly may be conveniently engaged with the pivot joint assemblies 22a and 22b by simply snapping it into place and just as conveniently removed by simply lifting the locking plate assembly away from the control plate 148.

Various types of resistance units may be employed in conjunction with the present invention to resist flexure or extension of the body joint or both flexure and extension as desired. A first resistance unit 36, illustrated in FIGS. 5 and 6, utilizes the shear resistance of a viscous fluid to resist the articulation of the frame 16 of the present invention. The resistance unit 36 includes a cuff shaped rotor 232 having a flat, circular end plate portion 234 and a cylindrical perimeter portion 236. The rotor 232 is disposed within a close fitting cavity 238 shaped to correspond to the shape of the rotor. The cavity 238 is in part defined by a circular stator assembly 240 composed of a stator member 242 stationarily mounted on the inside surface of the outside wall 244 of the outer housing 246 of the resistance unit 36. The stator 242 and the outside wall 244 may be constructed from a single unit or two separate units that are joined together. The remainder of the outer housing includes a cylindrical barrel or side wall portion 248 joined to an inside wall 250. Both the outside wall 244 and the inside wall 250 have an interior, circular pilot rim portion 252 which is ideally pressed into the inside diameter of the barrel portion 248 of the housing 246. A groove 254 is formed around the perimeter of the outside and inside walls 244 and 250 adjacent the pilot rim portions 252 for reception of a seal member, for instance an O-ring 256, to prevent leakage of the viscous fluid which entirely fills the portion of the cavity 238 not occupied by the rotor 232.

The resistance unit 36 includes a drive shaft 258 having an elongate pilot shaft portion 260 anti-frictionally journaled within a bushing 262 snugly engaged within a central blind bore formed in the stator 242. The pilot shaft portion 260 of the drive shaft 258 intersects a larger diameter shoulder portion 264 disposed through a clearance hole 266 formed in the central portion of inside wall 250. The rotor 234 is anti-rotationally fixed to the drive shaft 258 by a pin 267 extending through a close-fitting cross hole formed in the rotor end plate 234 to engage within a blind hole formed in the adjacent face of the rotor shoulder portion 264. A seal 268 is disposed within a counterbore 270 formed in the portion of the inside wall 250 facing the rotor 232 to provide a fluid-tight seal between the inside wall 250 and the outer diameter of the drive shaft shoulder portion 264. The drive shaft 258 also includes a male spline 272 disposed outwardly of the inside wall 250 to engage with the female spline 205 formed in the interior of the stub shaft 132, discussed above.

The resistance unit 36 is anti-rotationally mounted on the pivot joint assembly 22a by utilizing stub pins 206a and 208a which preferably are identical to stub pins 206 and 208, discussed above. Thus, as with the locking plate assembly 34, the resistance unit 36 may be conveniently engaged with the control plate 164 and support plate 148 in the same manner as the locking plate assembly 34, discussed above.

As noted above, the interior cavity 238 of the resistance unit 36 is filled with a highly viscous fluid. Ideally, the fluid has a viscosity of from about 500,000 to 1,000,000 centistoke and preferably is composed of silicone. This type of silicone fluid is commercially available from numerous sources. Due to the small clearances (typically between the 0.015 inch and the 0.050 inch) between the rotor 232 and the stationary components of the resistance unit 36, including the stator 242, the viscous fluid within the cavity 238 is sheared as the rotor is rotated, thereby providing resistance to the rotation of the rotor in either direction that the rotor may be rotated. Due to the substantial mass of the stator 242 and the relatively large surface area of the resistance unit housing 246, little heat build-up occurs in the viscous fluid, and thus the viscosity of the fluid remains substantially constant even if the apparatus 14 of the present invention is utilized over extended periods of time.

As will be appreciated, the resistance provided by unit 36 is a function of both the viscosity of the fluid within the cavity 238 and the surface area of the rotor 232, and especially the surface area of the perimeter portion 236 of the rotor. As such, the resistance to rotation provided by the resistance unit 36 may be varied by altering the viscosity of the fluid within the rotor cavity or by varying the width of the rotor, e.g., the width of the rotor perimeter portion 236. If the width of the rotor perimeter portion 236 is decreased from that shown in FIG. 6, the width of the housing 246 may also be correspondingly decreased which would advantageously reduce the overall width of apparatus 14 of the present invention.

Next referring to FIG. 8, a resistance unit 274 is illustrated which is similar to the resistance unit 230, but with the exception that a one-way roller clutch 275 is interposed between a drive shaft 276 and a disc-shaped rotor 277 encased within a housing 278 filled with a highly viscous fluid, of the same type used in unit 36, that is sheared as the rotor is rotated within the housing. A male spline 279 is fixed to the end of the drive shaft 276 extending outwardly of the housing 278 to engage with the female spline 206 of the stub shaft 132. Also, the resistance unit 274 is anti-rotationally mounted on the pivot joint assembly 22a by utilizing stub pins 206b and 208b which preferably are identical to stub pins 206 and 208, discussed above. Thus, as with the locking plate assembly 32 and the resistance unit 36, the resistance unit 274 also may be conveniently engaged with and disengaged from the control plate 164 and support plate 148.

It will be appreciated that by this construction of the resistance unit 274, rotation of the male spline 279 in one direction allows the drive shaft 276 to free wheel relative to the rotor 277 while rotation of the spline in the opposite direction causes the rotor to lock up and thus rotate with the drive shaft. It will be appreciated that the resistance unit 274 may be employed to impart resistance to the articulation of frame 16 when either flexing or extending the body joint while allowing free articulation of the frame in the opposition direction. Resistance in either extension or flexure may be desirable when recovering from certain types of injuries in which either the flexion or extension muscles are damaged but not both.

A further resistance unit 282 is illustrated in FIG. 9 which provides resistance to the articulation of the frame 16 in one direction about the pivot axis 24 while providing assistance in articulating the frame in the opposite direction. The resistance unit 282 may be helpful, for instance, when desiring to exercise the wearer's hamstrings when the wearer's quadricep muscles have atrophied after knee surgery or cannot be used due to their pull on a surgical repair. This is the case when the anterior cruciate ligament is repaired, for example. To this end, the resistance unit 282 includes an exterior circular housing 284 having end walls 286 and 288 capping the ends of the barrel portion 290 of the housing. The resistance unit includes a drive shaft 294 extending through the housing 284 and journaled within central openings formed in the end walls 286 and 288 of the resistance unit 282 or by any other convenient arrangement. One end of a torsion spring 296 is fixed to the drive shaft 294 by any convenient means, whereas the other end of the torsion spring is fixed to the inside surface of the barrel portion 290 of the housing 284. A male spline 300 is fixed to the end portion of the drive shaft 294 outwardly adjacent housing wall 288. The male spline 300 corresponds with the male splines 272 and 279 of the resistance units 36 and 274, respectively, and the male spline 204 of the locking plate assembly 34 to drivingly engage with the female spline 205 of the stub shaft 130, discussed above. As with the resistance unit 36, the resistance unit 282 also includes diametrically opposed stub pins 206c and 208c for mounting the resistance unit 282 on the articulating frame 16.

In operation, with the resistance unit 282 mounted in place, when the frame 16 is articulated in opposition to the torsion spring 296, a torque load must be applied about the pivot axis 24 to overcome the resistance of the torsion spring. However, when the torque load is terminated, the torsion spring 296 assists in articulating the frame 16 in the opposite direction. As noted above, this type of resistance unit would be helpful when desiring to exercise the hamstrings while recovering from an injury to the quadriceps. The torsion spring 296 would function to articulate a frame 16 in assistance to or in place of the quadricep muscles. It will be appreciated that the assistance provided by the torsion spring will depend upon various factors including the size of the spring and the number of coils composing the spring. Thus, torsion springs of different spring constants may be utilized in conjunction with the resistance unit 282.

The resistance unit 282 may be employed to impart a constant preload or force (preferably low level) on the body joint. This may be conveniently accomplished by prewinding the spring 296 by rotation of the male spline 30 before the male spline is engaged with the female spline 205, and the stub pins 206c and 208c are engaged with corresponding aligned bores 210 and 212 of the support plate 148. The preload on a torsion spring 296, by imparting a constant force on the body joint, may assist the wearer in regaining or increasing the range of motion of the joint, for instance after surgery to the joint. It is to be appreciated that a preloading device, similar to spring 296 or in other configurations may be incorporated into the other resistance units of the present invention.

FIG. 10 illustrates a measurement module 310 which may be employed to measure various parameters, such as the range of motion of the body joint, the speed at which the body joint is flexed and extended, and the torque being exerted by the body joint when articulating the frame 16. To this end, the measurement module 310 may be mounted on the outside of a resistance unit, for instance resistance unit 36, 274, or 282. The measurement module 310 includes a potentiometer (not shown) disposed with an outer housing 312 which is affixed to the exterior side of flat, thin, circular plate 314 having an outside diameter ideally corresponding to the outside diameter of the control plate 164 and the mounting plate 148. The measurement module includes an input shaft 316 extending through a central clearance hole formed in the plate 314 to securely engage with a male spline 318, which spline corresponds to the previously described male spline 204 of locking plate assembly 34, spline 272 of resistance unit 36 and spline 300 of resistance unit 282. Accordingly, the spline 318 engages within the female spline 205 formed in the stub shaft 130 to rotate the potentiometer through an arc corresponding to the angle of articulation of the frame 16. Potentiometers, of the type used with the measurement module 310 are standard articles of commerce.

The measurement module 310 is mounted on the frame 16 in a manner corresponding to the manner in which the resistance units, discussed above, and the locking plate assembly 34, as discussed above, are mounted on the frame. To this end, a pair of stub pins 206d and 208d extend transversely from plate 314 to extend through the clearance holes 214 and 216 formed in the control plate 164 to engage within the bores 210 and 212 formed in the mounting plate 148.

The output signal from the potentiometer 312 may be connected to a microprocessor through electrical leads 320 to determine various parameters, including the range of motion of the body joint being flexed, or exercised, the speed at which the joint is being flexed or extended, the torque load, if any, being overcome by the body joint as well as the work being accomplished by the body joint. The resistance torque may be provided by one of the resistance modules discussed above mounted on the other side of the frame 16.

Figure 11:
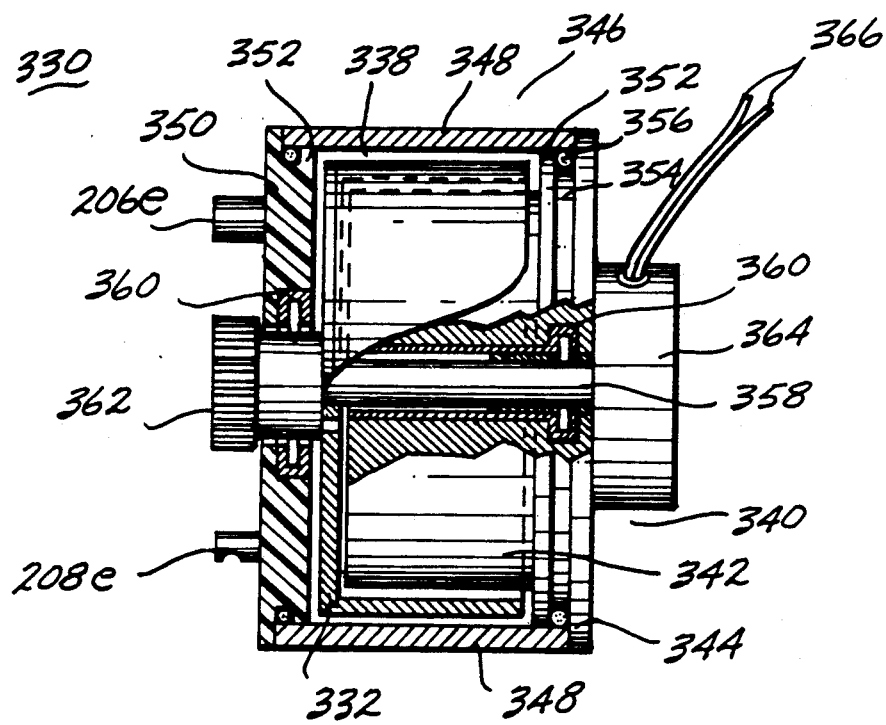
FIG. 11 is a cross-sectional view of a measurement module integrated into the structure of a resistance unit.

FIG. 11 illustrates a combined resistance unit and measurement module (transduced resistance unit) which is essentially an integration of the resistance unit 36 and the measurement module 310, both described above. The transduced resistance module 330 includes a cup-shaped rotor 332 similar to rotor 232, discussed above, disposed within a close fitting cavity 338 shaped to correspond to the shape of the rotor. The cavity 338 is in part defined by a circular stator assembly 340 composed of a stator member 342 stationarily mounted on the inside surface of the outside wall 344 of the outer housing 346 of the transduced resistance unit 330. As with stator assembly 240, the stator assembly 340 may be constructed as a single unit or two separate units (stator 342 and outside wall 244) joined together. The outer housing 346 also includes a cylindrical barrel or side wall portion 348 joined to an inside wall 350. Ideally, both the outside wall 344 and inside wall 350 have an interior, circular pilot rim portion 352 which is pressed into the inside diameter of the barrel portion 348 of the housing 346. A groove 354 is formed around the perimeter of the outside and inside walls adjacent the pilot rim portions 352 for reception of a seal member, for instance an O-ring 356, to prevent leakage of the viscous fluid which entirely fills the portion of the cavity 338 not occupied by the rotor 332.

The transduced resistance unit 330 includes a drive shaft 358 extending transversely through the center of the housing 346. The drive shaft is anti-frictionally mounted on combination bearing seals 360 snugly engaged within counterbores formed in the outside wall 334 and inside wall 350. The drive shaft 358 is antirotationally engaged with the rotor 332 by any convenient method. The end of the drive shaft extending beyond the inside wall 350 is connected to a male spline 362 sized to engage with the female spline 205 formed in the interior of the stub shaft 132, discussed above.

The opposite end of the drive shaft 358 is connected to a transducer, for instance a potentiometer (not shown), disposed within an outer housing 364 which is affixed to the exterior side of wall 344. As the male spline 362 rotates with the movement of frame 16, the potentiometer is moved through a corresponding arc thereby generating a related electrical signal which is transmitted through electrical leads 366 to a microprocessor (not shown). As with the measurement module 310, discussed above, the output signal from the transduced resistance unit 330 may be employed by the microprocessor to calculate various parameters to monitor the rehabilitative progress of the patient and also to provide feedback to the patient. This feedback may include the range of motion of the body joint being rehabilitated or exercised, the speed at which the body joint is flexed or extended, the torque load being overcome by the body joint and the work being expended by the body joint.

The transduced resistance unit 330 is mounted on the frame 16 in a manner corresponding to the manner in which the locking plate assembly 34, resistance units and measurement module 310, discussed above, are mounted on the frame. To this end, a pair of stub pins 206e and 208e extend transversely from inside wall 350 to extend through clearance holes 214 and 216 formed in the control plate 164 to engage within close fitting bores 210 and 212 formed in the mounting plate 148. It will be appreciated that the transduced resistance unit 330 may be mounted on one side of the frame 16 and a similar resistance unit, perhaps without the transducer, may be mounted on the opposite side of the frame. By loading both sides of the frame 16, an unequal torque load is not imposed on one side of the frame which might occur if a resistance unit were utilized on only one side of the frame.

It will also be appreciated that a transducer, e.g., a potentiometer, may be incorporated with each of the different types of resistance units discussed above, including resistance units 36, 274, and 282.

As illustrated in FIG. 13, the exercise apparatus 14 of the present invention may be utilized as a component of an ergometer 370 to calculate the work being expended by the exerciser as well as other parameters, thereby to monitor the progress of the rehabilitation or exercise program and provide instantaneous feedback to the user. In the ergometer 370, the output signal from the transducer, for instance, the transducer associated with resistance unit 330, is transmitted to an integrated circuit 372 located within a small, portable, hand-held housing 374 illustrated in FIG. 12. The housing 374 is detachably connectable to the transduced resistance unit 330 by the electrical leads 336, which preferably are coiled to be readily extendable and retractable. The integrated circuit 372 includes of a microprocessor 376, an A/D converter 378 disposed between the microprocessor and the transduced resistance unit 330 and a memory unit 380, which preferably is composed of an EEPROM for storing the data received from the transduced resistance unit 330.

The integrated circuit 372 also includes a real time clock and calendar 382 for use in analyzing the data from the transduced resistance unit 330 as a function of time, for instance, to calculate the relative speed of movement of the frame sections 18 and 20 about the pivot axis 22 under the control of a program stored in a memory unit 384, preferably in the form of a ROM. Another value that may be calculated by the ergometer 370 of the present invention is the torque being expended by the user when articulating the two frame sections relative to each other. This information, as well as the relative speed at which the frame unit is being articulated, is transmitted to the user on a display 386. Other information, such as the number of cycles that the present invention has used (for instance, composed of flexure and then extension of a body joint), may be determined by the microprocessor 376 and transmitted to the user in a second display 388.

Figure 12:
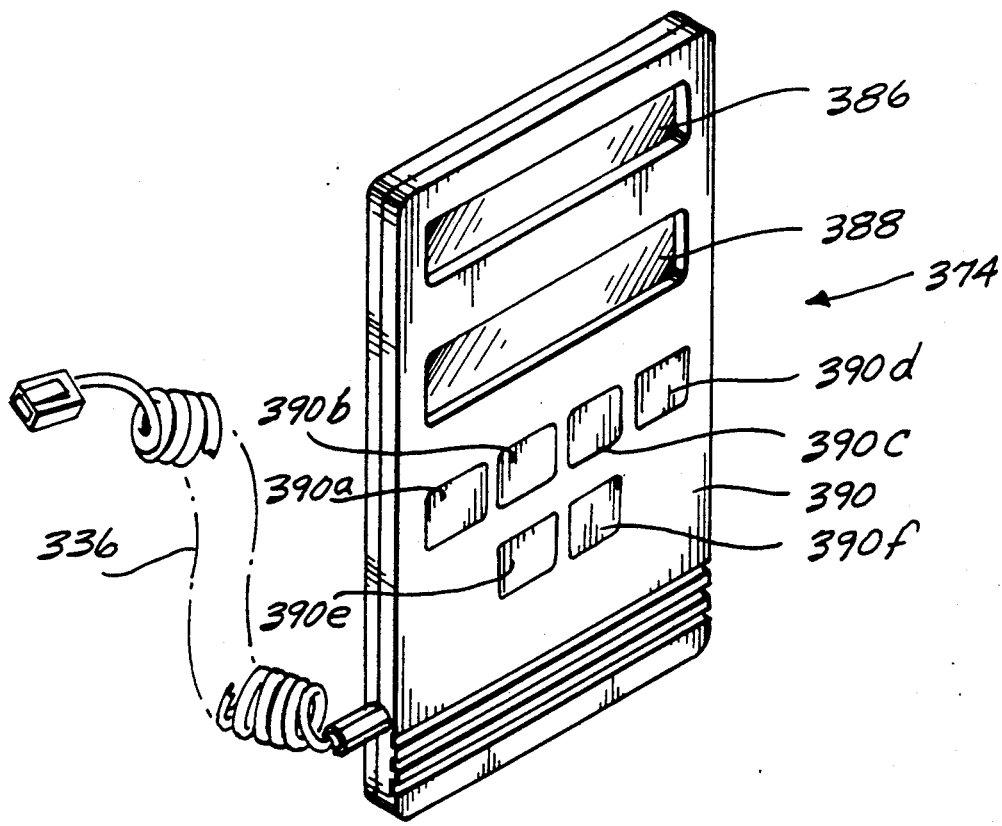
FIG. 12 is an isometric view of a hand-held data recorder and microprocessor unit that is detachably connectable to a measurement module to cooperatively function with the other components of the present invention as an ergometer; and, FIG. 13 is a schematic diagram of the ergometer of the present invention.

The particular calculations made by the ergometer 370 and displayed on the displays 386 and 388 may be controlled by the user by operation of a key pad 390 having various pressure actuated switches 392a, 392b, 392c, 392d, 392e and 392f, as illustrated in FIGS. 12 and 13. The switch 390a is depressed when desiring to show the relative rotational speed of the frame sections 18 and 20 about the pivot axis 20 on display 386, whereas switch 390b is depressed when desiring to show the torque being expended by the user of the apparatus 14. Switch 392c is utilized when setting the clock/calendar 382 to the correct time. Switch 390d is depressed when resetting the display 388 which shows the number of repetitions that the exerciser or physical therapy patient has accomplished. The "select" and "set" switches 390f and 390e are used to input various factors or information that is used in the calculations performed by the microprocessor 376. This information may include, for instance, the type of resistance unit being used on apparatus 14, the size of the resistance unit, the size of the apparatus 14 (It is contemplated that the apparatus may be manufactured in different sizes.), the position of the extension member 114 relative to the lower arm 110, etc. Other information that may be inputted includes, for example, the identity (name) of the user of the apparatus 14 as well as the sex and age of the user.

Periodically, the integrated circuit 372 may be interfaced with a personal computer 394 through an appropriate interface 396 to down load the information stored in the memory unit 380 for the long-term storage of this data on a different type of memory device 398, such as a floppy disk or hard disk. In addition, the data transferred from the memory unit 380 may be analyzed with the computer 394 using more sophisticated techniques than capable with data processor 376, thereby to monitor the rehabilitative progress of the patient or to monitor the progress of the exercise regime being undertaken by the user. It will be appreciated that by incorporating the integrated circuit 372 in a small, portable housing 374, the present invention may be utilized at virtually any location and the data recorded and simultaneously initially analyzed by the ergometer 370 and then later analyzed by a larger processor located at a stationary location, for instance, at the office of a physical therapist or doctor.

It will also be appreciated that the integrated circuit 372 may be utilized not only with the transduced resistance unit 330 shown in FIG. 11, but also with the measurement module shown in FIG. 10. Further, the integrated circuit can be employed with other types of transducers, such as a wheatstone bridge or an "electric eye".

As will be apparent to those skilled in the art to which the invention is addressed, the present invention may be embodied in forms other than those specifically disclosed above and may be adapted for use with other body joints, such as the ankle or wrist joints without departing from the spirit or scope of the present invention. The particular embodiments of the exercise apparatus 14 set forth above are therefore to be considered in all respects as illustrative and not restrictive. The scope of the present invention is as set forth in the appended claims rather than being limited to the examples of the combination brace and wearable exercise apparatus set forth in the foregoing description.

The embodiments of the invention in which an exclusive property or privilege is claimed are defined as follows:

1. An adjustable combination brace and wearable exercise apparatus to selectively render a body joint immovable, to control the movement of the body joint through a desired range of motion, and to exercise the muscles associated with the body joint as the body joint is moved through the controlled range of motion, comprising:
   a) a first pivot arm;
   b) first means to operably connect the first pivot arm to a first limb of a body joint;
   c) a second pivot arm;
   d) second means to operably connect the second pivot arm to a second limb of the body joint; and,
   e) a pivot joint assembly, comprising:
      (i) first means pivotally interconnecting the first and second pivot arms about a pivot axis generally coinciding with the anatomical pivot axis of the associated body joint;
      (ii) second means selectively controlling the permissible range of angular motion between the first and second pivot arms from substantially no relative angular motion to relative angular motion sufficient to permit the body joint to move between a substantially fully flexed position and a substantially fully extended position; and,
      (iii) third means for operably fastening replaceable resistance means thereto to impose a desired level of resistance to the relative rotation of the first and second pivot arms in either or both relative rotational directions about the pivot axis of the pivot joint assembly and without requiring disassembly of the pivot joint assembly or replaceable resistance means to releasably engage or disengage the resistance means with the pivot joint assembly.

2. The adjustable combination brace and wearable exercise apparatus according to claim 1, wherein the second means selectively controlling the range of motion between the first and second pivot arms includes a control plate mounted on one of the two pivot arms, the control plate having portions adapted for receiving stop means at selected locations about the control plate, with the location of the stop means on the control plate determining the range of anular motion allowed between the first and second pivot arms.

3. The adjustable combination brace and wearable exercise apparatus according to claim 2, further comprising a detachable lock-up structure mounted on the control plate and having portions engageable with the arm other than the arm on which the control plate is mounted thereby to prevent relative rotation between the two arms.

4. The adjustable combination brace and wearable exercise apparatus according to claim 2, wherein:
   a) the first and second pivot arms having overlapping end portions comprising part of the pivot joint assembly; and,
   b) means for mounting the control plate on the end portion of one of the two pivot arms to overlap the side of the other pivot arm facing away from the pivot arm on which the control plate is mounted thereby sandwiching the end portion of the other pivot arm between the end portion of the pivot arm on which the control plate is mounted and the control plate.

5. The adjustable combination brace and wearable exercise apparatus according to claim 4, further comprising a lock-up plate structure anti-rotationally mounted on the overlapping portion of one of the first and second pivot arms, the lock-up plate structure having portions engageable with the other of the first and second pivot arms to prevent relative rotation of the first and second pivot arms.

6. The adjustable combination brace and wearable exercise apparatus according to claim 1, further comprising a lock-up structure mounted on one of the two pivot arms and having portions engageable with the other of the two pivot arms to prevent relative rotational movement between the two pivot arms.

7. The adjustable combination brace and wearable exercise apparatus according to claim 1, further comprising transducer means mounted on the apparatus and operably associated with the pivot joint assembly to monitor the relative positions of and relative movement between the first and second pivot arms.

8. The adjustable combination brace and wearable exercise apparatus according to claim 1, further comprising resistance means received by the third means for operably fastening replaceable resistance means, the resistance means comprising:
   a) a stator stationarily associated with one of the two pivot arms;
   b) a rotor coupled to the other of the two pivot arms to rotate relative to the stator; and,
   c) resistance means imparting a drag load between the rotor and stator that must be overcome to rotate the first and second pivot arms relative to each other.

9. The adjustable combination brace and wearable exercise apparatus according to claim 8, wherein the resistance means includes one-way clutch means operably interposed between the rotor and the pivot arm to which the rotor is connected to drivingly engage the rotor and associated pivot arm when the associated pivot arm is rotated in a first direction to the second pivot arm and to permit the rotor and the associated pivot arm to free wheel relative to each other when the associated pivot arm is rotated in the opposite direction relative to the second pivot arm.

10. The adjustable combination brace and wearable exercise apparatus according to claim 1, wherein the resistance means includes resistance and energy storage means providing resistance to the rotation of the first and second pivot arms from nominal positions in a first relative direction and storage of the energy required to overcome the resistance, and then providing assistance in rotating the first and second pivot arms in the reverse relative direction tending to return the first and second pivot arms toward their nominal positions when the force imposed on the pivot arms to rotate the pivot arms in the first relative direction is terminated.

11. The adjustable combination brace and wearable exercise apparatus according to claim 10, wherein the resistance means imparts a nominal preload on the first and second pivot arms tending to rotate the first and second pivot arm in the first relative direction.

12. The adjustable combination brace and wearable exercise apparatus according to claim 10, wherein the resistance means includes an elastic member which is displaced from its nominal condition when the first and second pivot arms are moved in the first relative direction by the body joint, and which tends to return to its nominal condition when the load imposed on the first and second pivot arms by the body joint is terminated.

13. The adjustable combination brace and wearable exercise apparatus according to claim 12, wherein the resistance means imparts a nominal preload on the first and second pivot arms tending to rotate the first and second pivot arms in the first relative direction.

14. The adjustable combination brace and wearable exercise appartus according to claim 12, wherein the elastic member includes a spring member.

15. The adjustable combination brace and wearable exercise apparatus according to claim 14, wherein the spring member includes a torsion spring.

16. The adjustable combination brace and wearable exercise apparatus according to claim 1, wherein the pivot joint assembly further comprises fourth means for nominally applying a preload on the first and second pivot arms tending to rotate the first and second pivot arms about the pivot axis in one relative direction.

17. The adjustable combination brace and wearable exercise apparatus according to claim 1, wherein the first attachment means includes a first cuff assembly connected to the first pivot arm to detachably encircle the first limb of the body joint and the second connection means includes a second cuff assembly attached to the second pivot arm to detachably encircle the second limb of the body joint.

18. The adjustable combination brace and wearable exercise apparatus according to claim 17, wherein at least one of the first and second cuff assemblies is pivotally attached to its respective pivot arm to enable the cuff assembly to pivot about an axis extending generally transversely to the length of the body limb being encircled by the cuff assembly.

19. The adjustable combination brace and wearable exercise apparatus according to claim 17, wherein the resistance means includes an elastic member which is displaced from its nominal condition when the first and second pivot arms are moved in the first relative direction by the body joint, and which tends to return to its nominal condition when the load imposed on the first and second pivot arms by the body joint is terminated.

20. The adjustable combination brace and exercise apparatus according to claim 17, further comprising means for mounting at least one of the first and second cuff assemblies on its respective pivot arm to enable the cuff assembly to freely slide a prescribed distance along its respective pivot arm.

21. The adjustable combination brace and wearable exercise apparatus according to claim 17, wherein at least one of the first and second cuff assemblies is composed of two spaced-apart cuffs to encircle the associated body limb at two locations along the corresponding pivot arm.

22. The adjustable combination brace and wearable exercise apparatus according to claim 21, further comprising means for mounting at least one of the cuffs on its corresponding pivot arm to freely slide a prescribed distance along the length of the pivot arm.

23. A combination brace and wearable exercise apparatus to selectively restrain a body limb against movement, to allow the body limb to move through a controlled range of motion about the anatomical pivot axis of the body limb, and to apply a desired level of resistance to the movement of the body limb, the combination brace and wearable exercise apparatus comprising:
   a) a first frame section having first means to operably connect the first frame section to a first limb of a body joint;
   b) a second frame section having second means to operably connect the second frame section to the second limb of the body joint; and,
   c) a pivot joint assembly, comprising:
      (i) first means pivotally interconnecting the first and second frame sections about a pivot axis generally coinciding with the anatomical pivot axis of the associated body joint;
      (ii) second means selectively controlling the permissible relative articulation of the first and second frame sections to selectively vary the maximum permitted extension and maximum permitted flexion of the body joint; and,
      (iii) third means for fastening replaceable load means thereto to impart a desired level of resistance that must be overcome to enable the first and second frame sections to rotate about the pivot axis of the pivot joint assembly in either or both relative directions and without requiring disassembly of the pivot joint assembly or replaceable to releasably engage or disengage the resistance means load means with the pivot joint assembly.

24. The combination brace and wearable exercise apparatus according to claim 23, wherein the second means selectively controlling the articulation of the first and second frame sections includes a control plate on one of the two frame sections, the control plate having portions adapted for receiving stop members at selected locations about the control plate, with the location of the stop members on the control plate determining the range of angular motion permitted between the first and second frame sections.

25. The combination brace and wearable exercise apparatus according to claim 24, wherein:
   a) the first and second frame sections having overlapping portions comprising part of the pivot joint assembly; and,
   b) means for mounting the control plate on one of the two frame sections to overlap the side of the other frame section overlapping portion facing away from the frame section on which the control plate is mounted thereby sandwiching the overlapping portion of the other frame section between the overlapping portion of the frame section on which the control plate is mounted and the control plate.

26. The combination brace and wearable exercise apparatus according to claim 23, wherein the pivot joint assembly further comprises fourth means detachably engagable with the pivot joint assembly for securely retaining the first and second pivot arms in fixed relative position.

27. The combination brace and wearable exercise apparatus according to claim 26, wherein the fourth means includes a lock-up plate structure mountable on one of the two frame sections, the lock-up plate structure having portions engagable with the other of the two frame sections for preventing relative rotation between the two frame sections.

28. The combination brace and wearable exercise apparatus according to claim 23, further comprising transducer means associated with the pivot joint assembly for sensing the relative angular locations about the pivot axis of the first and second frame sections.

29. The adjustable combination brace and wearable exercise appartus according to claim 23, further comprising load means received by the third means for fastening replaceable load means, the load means comprising:
   a) a stator mounted on one of the two frame sections;
   b) a rotor coupled to the other of the two frame sections to rotate relative to the stator; and,
   c) resistance means imparting a drag load between the rotor and stator that must be overcome to rotate the first and second frame sections relative to each other.

30. The adjustable combination brace and wearable exercise apparatus according to claim 29, further comprising tranducer means incorporated into the structure of the load means to monitor the relative angular positions of the first and second frame sections about the pivot axis.

31. The adjustable combination brace and wearable exercise apparatus according to claim 30, wherein the load means further includes means for applying a nominal preload between the first and second frame sections tending to rotate the first and second frame sections in the first relative direction.

32. The adjustable combination brace and wearable exercise apparatus according to claim 23, wherein the first attachment means includes a first cuff assembly connected to the first frame section to detachably encircle the first limb of the body joint and the second connection means includes a second cuff assembly attached to the second frame section to detachably encircle the second limb of the body joint.

33. The adjustable combination brace and wearable exercise appartus according to claim 32, wherein at least one of the first and second cuff assemblies is pivotally attached to its respective frame section to enable the cuff assembly to pivot about an axis extending transversely to the length of the body limb being encircled by the cuff assembly.

34. The adjustable combination brace and wearable exercise apparatus according to claim 32, further comprising means for mounting one of the first and second cuff assemblies on its corresponding frame section to enable the cuff assembly to slide relative to the pivot axis, including when the first and second frame sections are pivoted relative to each other about the pivot axis.

35. The adjustable combination brace and wearable exercise apparatus according to claim 23, wherein:
   the first frame section includes a pair of laterally spaced apart first pivot arms having end portions operably associated with the pivot joint assembly; and,
   the second frame section having a pair of laterally spaced apart second pivot arms having end portions each adjacent a corresponding end portion of a first arm and operably associated with the pivot joint assembly;
   the pivot joint assembly first means pivotally interconnecting the ends of the first pivot arms with adjacent ends of the corresponding second pivot arms whereby the first pivot arms pivot relative to the second pivot arms about a pivot axis generally coinciding with the anatomical pivot axis of the associated body joint;
   the pivot joint assembly second means selectively controlling the permissible relative articulation of corresponding first and second pivot arms about the pivot axis to selectively vary the maximum extension and maximum flexion of the body joint; and,
   the pivot joint assembly third means associated with both sets of the first and second pivot arms to receive replaceable load means to impart a desired level of resistance that must be overcome to enable the first and second pivot arms to rotate about the pivot axis of the pivot joint assembly in either or both relative directions and without requiring disassembly of the pivot joint assembly to engage or disengage the resistance means from the pivot joint assembly.

36. The combination brace and wearable exercise apparatus according to claim 35, wherein the second pivot joint assembly means includes a control plate mounted on one of the two pivot arms of each set of associated first and second pivot arms, the control plate having portions adapted to receive stop members at selected locations about the control plate, with the location of the stop members on the control plate determining the range of angular motion permitted between corresponding first and second arms.

37. The combination brace and wearable exercise apparatus according to claim 36, wherein:
   the corresponding first and second pivot arms having overlapping end portions comprising part of the pivot joint assembly; and,
   means for mounting the control plate on the end portion of one of the two associated pivot arms to overlap the side of the other pivot arm facing away from the pivot arm on which the control plate is mounted thereby sandwiching the end portion of the other pivot arm between the overlapping portion of the pivot arm on which the control plate is mounted and the control plate.

38. The combination brace and wearable exercise apparatus according to claim 35, further comprising a lock-up plate structure associated with the pivot joint assembly and mountable on one of the pivot arms of the first and second frame sections, said lock-up plate structure having means for engaging the corresponding pivot arm of the other of the first and second frame sections to retain the first and second associated pivot arms in a fixed position relative to the pivot axis.

* * * * *

UNITED STATES PATENT AND TRADEMARK OFFICE
CERTIFICATE OF CORRECTION

PATENT NO. : 5,052,379
DATED : October 1, 1991
INVENTOR(S) : J.F. Airy et al.

It is certified that error appears in the above-indentified patent and that said Letters Patent is hereby corrected as shown below:

| COLUMN | LINE | |
|---|---|---|
| 1 | 9 | "split" should be --splint-- |
| 7 | 5 | "coresponding" should be --corresponding-- |
| 15 | 21 | "signal" should be --signals-- |
| 19 | 26 | "appartus" should be --apparatus-- |
| 20 | 38 & 39 | after "replaceable" insert --resistance means-- |
| 20 | 40 | after "disengage the" delete "load means". |
| 21 | 16 | "appartus" should be --apparatus-- |
| 21 | 29 | "tranducer" should be --transducer-- |

UNITED STATES PATENT AND TRADEMARK OFFICE
CERTIFICATE OF CORRECTION

PATENT NO. : 5,052,379
DATED : October 1, 1991
INVENTOR(S) : J.F. Airy et al.

Page 2 of 2

It is certified that error appears in the above-indentified patent and that said Letters Patent is hereby corrected as shown below:

| COLUMN | LINE | |
|---|---|---|
| 21 | 48 | "appartus" should be --apparatus-- |

Signed and Sealed this

Twenty-fifth Day of October, 1994

Attest:

BRUCE LEHMAN

*Attesting Officer*    *Commissioner of Patents and Trademarks*